United States Patent
Dangin et al.

(10) Patent No.: US 6,544,515 B1
(45) Date of Patent: Apr. 8, 2003

(54) ACCELERATION OF THE RATE OF DIGESTION OF A PROTEIN

(75) Inventors: Martial Dangin, Clermont-Ferrand (FR); Clara Lucia Garcia-Rodenas, Mollie-Margot (CH); Bernard Beaufrere, Chamalières (FR); Olivier Ballevre, Lausanne (CH)

(73) Assignee: Nestec S.A., Vevey (CH)

( * ) Notice: Subject to any disclaimer, the term of this patent is extended or adjusted under 35 U.S.C. 154(b) by 215 days.

(21) Appl. No.: 09/588,650

(22) Filed: Jun. 7, 2000

Related U.S. Application Data (63) Continuation of application No. PCT/EP98/07334, filed on Nov. 12, 1998.

(30) Foreign Application Priority Data

Dec. 8, 1997 (EP) ............................................ 97203840

(51) Int. Cl.⁷ .............................................. A61K 38/53
(52) U.S. Cl. ........................ 424/94.5; 424/94.1; 514/54
(58) Field of Search ........................... 514/54; 424/94.5, 424/94.1

(56) References Cited

U.S. PATENT DOCUMENTS 5,126,332 A * 6/1992 Ohta et al. .................... 514/54
5,279,839 A 1/1994 Gottmann et al. ............ 426/20

FOREIGN PATENT DOCUMENTS

| EP | 0 725 145 | 10/1996 |
| JP | 725145 A1 * | 8/1996 |
| WO | WO 93/22930 | 11/1993 |
| WO | WO 97/05785 | 2/1997 |

* cited by examiner

*Primary Examiner*—Dwayne C. Jones
(74) *Attorney, Agent, or Firm*—Winston & Strawn (57) ABSTRACT

The invention thus relates to a method for accelerating the rate of digestion of a protein matter, in which a protein matter is treated with transglutaminase, and it is mixed with anionic polysaccharides. The invention also relates to the use of the rapidly digested protein matter for preparing a food or pharmaceutical composition intended for oral administration to a mammal, to induce a postprandial peak of plasmatic increase in amino acids. This composition is intended for modulating the postprandial protein gain, limiting the problems linked to gastrointestinal motility disorders, limiting the postprandial sensations of nausea in pregnant women, and/or limiting the postprandial risks of regurgitation and/or gastro-esophageal reflux. Finally, a subject of the invention is also a food or pharmaceutical composition comprising anionic polysaccharides and a protein matter treated with transglutaminase.

20 Claims, 3 Drawing Sheets

ACCELERATION OF THE RATE OF DIGESTION OF A PROTEIN

CROSS-REFERENCE TO RELATED APPLICATIONS

This application is a continuation of the U.S. National Stage designation of co-pending International Patent Application PCT/EP98/07334, filed Nov. 12, 1998, the content of which is expressly incorporated by reference herein.

FIELD OF THE INVENTION

The subject of the invention.is a method for accelerating the rate of digestion of a protein, and the use of a protein thus modified for preparing a food or pharmaceutical composition for modulating the postprandial plasmatic level of amino acids.

BACKGROUND OF THE INVENTION

In humans, during a nycthemeron, food intake is discontinuous. Postprandial periods, i.e. the phases of nutrient assimilation from the digestive tract, alternate with periods of physiological fast. These diurnal variations in the nutritional status affect the components of protein metabolism, and consequently the protein balance.

Thus, the consumption of proteins results in an increase in the plasmatic level of amino acids (Aoki et al., Am. J. Olin. Nutr., 41, 1–18, 1987). Similarly, the elevation of the plasmatic level of amino acids is associated with a decline in proteolysis and a stimulation of the oxidation of amino acids and of protein synthesis (Castellino et al., Am. J. Physiol., 262, 162–176, 1992; Giordano et al., Diabetes, 45, 393–399, 1996; Clugston et al., Olin. Nutr., 36, 57–70, 1982; Motil et al., Am. J. Physiol., 240, E712–721, 1981; Melville et al., Metabolism., 30, 248–255, 1989; Pacy et al., Olin. Sci., 86, 103–118, 1994).

The protein balance, which is negative during the period of physiological fast, becomes positive during the postprandial period. The relative extent of each phase therefore determines the evolution of the protein mass of the body. It is thus essential to be able to magnify the postprandial protein gain in order to optimize the evolution of the protein mass in numerous circumstances.

Recently, Boirie et al. have shown, in healthy young volunteers, that the postprandial protein gain depends on the rate of digestion of the ingested proteins (delay between the ingestion and the absorption of the nutriments by the body), this phenomenon being linked to the structure of the proteins. Lactoserum administered in a single oral dose induces a very early appearance in the blood of amino acids of food origin, the effect of which is a peak of plasmatic concentration of amino acids. A clear stimulation of protein synthesis and of oxidation of leucine is also observed. These postprandial modifications lead to a considerable improvement in the protein gain with respect to the period of physiological fast (Boirie et al., Am. J. Physiol., 271, E1083–1091, 1996).

In comparison with lactoserum, the amino acids which are derived from casein are absorbed progressively over a longer period. In this case, the plasmatic concentration of amino acids rises moderately, but this rise persists with time, several hours after a meal (Boirie et al., Nutr. Olin. Metabol., 9, 171, 1995).

The rate of digestion is thus different between these two types of protein, lactoserum thus being classified among the rapidly digested proteins, and casein being classified among the slowly digested proteins.

The behavior of rapidly digested proteins can be exploited for the nutrition of subjects with a considerable and immediate physiological requirement for amino acids, to maintain their body mass, such as patients who have just had a surgical operation (Arnold et al., Nutr. Olin. Metabol., 6, 3–12, 1992); children (Dewey et al., Eur. J. Olin. Nutr., 50, supplement 1, S119–150, 1996); or sportspersons, in particular after a physical effort, for example (Biolo et al., Am. J. Physiol., 273, E122–129, 1997; Rennie et al., In Physical Activity, Fitness and Health: Physical Activity & Protein Metabolism, Bouchard et al., Champaign, Ill., Human kinetics, 432–450, 1994).

Rapidly digested proteins can also be exploited for the nutrition of subjects with nausea, vomiting, and/or a sensation of satiety that is too strong and protracted after a meal, such that they experience discomfort, or even difficulties, in eating regularly and/or sufficiently. The people concerned can be subject to passing nausea, such as pregnant women; or can have gastrointestinal motility disorders, in particular elderly people and people with a pathological state such as anorexia, diabetes, the presence of a gastric carcinoma, neurological disorders (e.g., Parkinson's disease), drug or alcohol dependency, etc., for example (Maes et al., in $^{13}CO_2$ Breath test at the laboratory: Digestion-Absorption, Y. Groos Ed., p.55–69, 1996).

Rapidly digested proteins can also be exploited for limiting the risks of regurgitation and/or gastro-esophageal reflux, in particular in infants, premature babies, pregnant women or patients fed by the enteral route (Fried et al., J. Pediatr., 120, 569–572, 1992).

To date, it has never been proposed to accelerate the rate of digestion of a protein, in particular in order to modulate the postprandial plasmatic level of amino acids, and as a result to modulate the postprandial protein gain, and/or to limit the postprandial sensations of nausea in pregnant women, and/or to limit the problems linked to gastrointestinal motility disorders and/or to limit the postprandial risks of regurgitation and of gastro-esophageal reflux.

In addition, some slowly digested proteins, such as casein, can have a high nutritive value, i.e. a balanced and high content of each of the amino acids which are essential for the body, such as lysine, tryptophan, leucine, isoleucine, valine, phenylalanine, methionine and threonine, for example. Unfortunately, the nutritive value of these proteins is not sufficiently exploited in people with a physiological requirement for rapidly digested proteins.

Certain treatments of proteins are already known for modifying their rate of digestion. For example, WO97/05785 (Milupa GmbH) indicates that treating proteins, in particular milk casein, with transglutaminase makes it possible to slow their rate of digestion. Transglutaminase (EC2.3.2.13), also known as Factor XIIIa, y-glutamyltransferase or fibrinoligase, is known to modify proteins by catalyzing polymerization, deamidation, and amine-incorporation reactions (Nielsen, Food biotechnol., 9, 119–156, 1995).

Similarly, soluble dietary fibers are known to increase the viscosity of the gastrointestinal content, and thus the time for hydrolysis and absorption of sugars (Cameron-Smith et al., Br. J. Nutr., 71, 563–571, 1994). In the same way, U.S. Pat. No. 5,126,332 (Terumo Kabushiki Kaisha) advocates mixing casein with carrageenans or a guar gum so as to form a gel in the stomach, which will be slowly broken up in the intestine, to slow the absorption of sugars, and probably also of casein, and thus to prevent a rapid increase in glucose in the blood of diabetics.

Finally, another efficient means for accelerating the rate of digestion of proteins generally consists in carrying out an extensive hydrolysis, until hydrolysis residues are obtained which are less than 10,000 Daltons, for example. To this end, U.S. Pat. No. 5,039,532 describes a method in which whey is subjected to a partial enzymatic hydrolysis by means of proteolytic enzymes, it is subjected to a heat treatment to denature the minor proteins, thus rendering them accessible to a subsequent enzymatic degradation, it is cooled and is then subjected to a second hydrolysis and heat treatment again to inactivate the enzyme (see also EP 96202475.8; EP 629350; JP 3-18168; Beaufrere et al., Am. J. Physiology, 30, E907–E914, 1994).

The present invention is directed to assisting in satisfying the nutritive requirements of certain categories of people, with proteins which are initially slowly digested proteins, and which have been transformed into rapidly digested proteins.

SUMMARY OF THE INVENTION

The invention thus is directed to compositions and methods involving the digestion of protein matter. One aspect of the present invention relates to a method for accelerating the rate of digestion of a protein matter, in which the protein matter is treated with transglutaminase and mixed with anionic polysaccharides. Compositions of the treated protein matter also represent yet another aspect of the invention.

Other aspects of the present invention include methods of modulating postprandial protein gain in mammals, reducing problems linked to gastrointestinal motility disorders in mammals, limiting nausea in pregnant women, and limiting risk of regurgitation and/or gastro-esophageal reflux in mammals. These methods may all be accomplished by oral administration of a composition comprising rapidly digested protein matter, i.e., protein matter which, when ingested by rats weighing from 140 grams to 200 grams, leads to a disappearance of half the ingested nitrogen present in the digestive tract in less than 70 minutes. To achieve this, the protein matter is pretreated so as to transform slowly digested proteins that it contains into rapidly digested proteins which have at least substantially conserved the same initial molecular weight. These methods can advantageously incorporate protein matter, the digestion rate of which can be accelerated, as stated above, through treatment of the protein matter with transglutaminase and mixing with anionic polysaccharides.

The anionic polysaccharides used in any or all of these methods can be alginates, xanthan, gum arabic, pectins, kappa-carrageenans, iota-carrageenans, lambda-carrageenans, carboxymethylcellulose, sulfated dextrans, gellan gum, or mixtures thereof. Preferably, the protein matter used in any or all of these methods may include milk proteins.

Additionally, the protein matter included or initially contained in any or all of these methods can include slowly digested proteins, i.e., proteins which, when ingested by rats weighing from 140 grams to 200 grams, lead to a disappearance of half the ingested nitrogen present in the digestive tract in more than 80 minutes. In a preferred embodiment, the treatment of the protein matter with transglutaminase and the addition of anionic polysaccharides are such that the protein matter thus treated, when ingested by rats weighing from 140 grams to 200 grams, leads to a disappearance of half the ingested nitrogen present in the digestive tract in less than 70 minutes.

Another aspect of the present invention is directed to a food or pharmaceutical composition including anionic polysaccharides, protein matter treated with transglutaminase, or a combination thereof.

DETAILED DESCRIPTION OF THE PREFERRED EMBODIMENTS

Contrary to all expectations, the rate of digestion of a protein can be accelerated without previously carrying out its hydrolysis. Similarly, despite past convictions, proteins which are treated with transglutaminase and/or proteins to which anionic fibers are attached have an accelerated rate of digestion. WO 97/05785 (Milupa GmbH) claimed, without demonstrating it, that treating proteins, in particular milk casein, with transglutaminase made it possible to slow their rate of digestion. Similarly, as dietary fibers increase the viscosity of the gastrointestinal content, it was estimated that the time for digestion of all the nutrients present in a meal containing these fibers had, therefore, to be increased (see U.S. Pat. No. 5,126,332).

Finally, the treatments according to the invention, which aim to accelerate the rate of digestion of proteins, did not take place to the detriment of the digestibility of the proteins. The proteins thus treated do not therefore substantially induce an increase in the ratio calculated between the amount of protein ingested orally and the amount of protein absorbed by the body (as an example, see Vaughan et al., Am. J. Olin. Nutrition, 30, 1709–1712, 1977).

In the context of the present invention, "substantially" means within 10%, preferably within 5%, more preferably within 2%.

Figure 3:
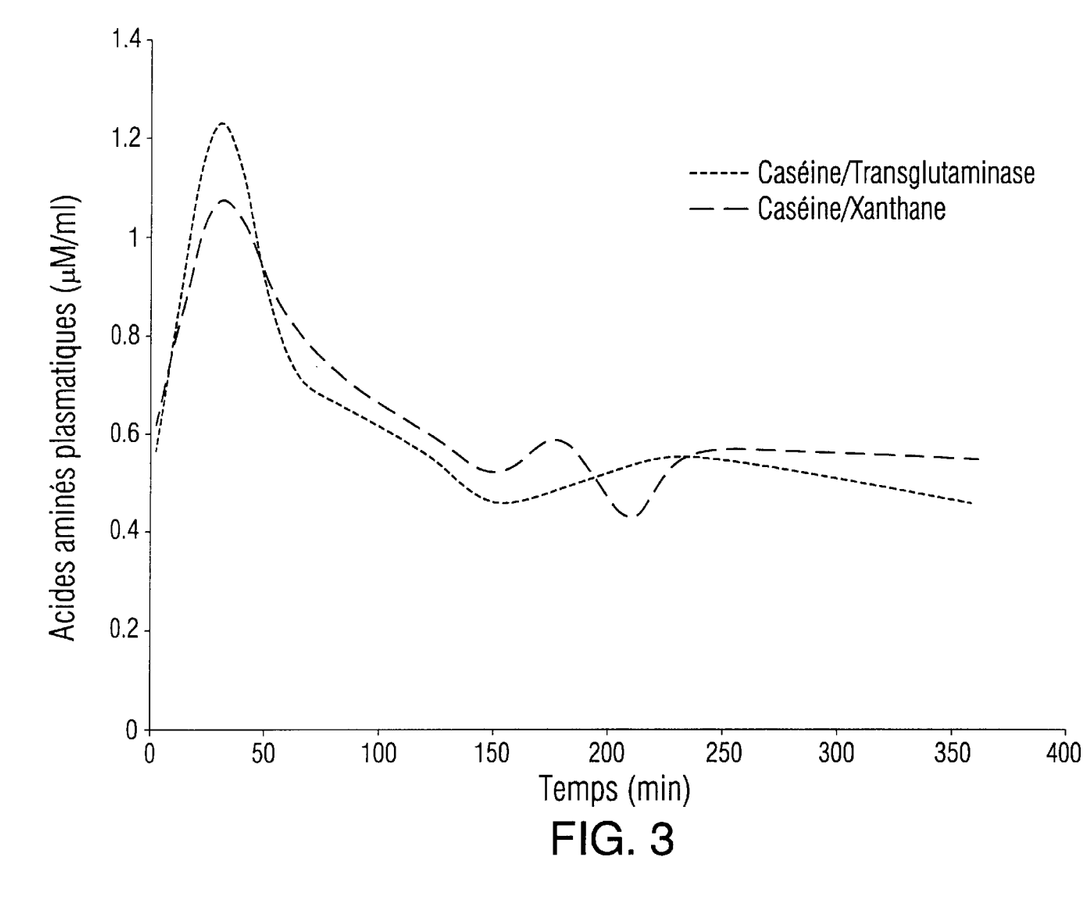
FIG. 3 represents the evolution of the amino acid content in the blood, as a function of time, in rats fed on casein treated with transglutaminase or on a mixture of native casein and xanthan.

In the context of the present invention, the expression "plasmatic postprandial peak of amino acids" corresponds to a rapid and noticeable increase in the plasmatic level of amino acids after a meal, followed by a decrease which is virtually as rapid (see FIG. 3).

To implement the present method, a protein matter is used, i.e. all kinds of matter comprising proteins, whether they are of animal, plant or microbial origin, in particular proteins from milk, oilseeds, legumes, egg yolk, or brewer's yeast, for example.

Milk is intended firstly to refer to a milk of animal origin, such as the milk of a cow, goat, sheep, buffalo, zebra, horse, ass, camel, and the like. The term milk also applies to what is commonly called a vegetable milk, i.e. an extract of treated or untreated vegetable matters, such as legumes (soybean, chickpea, lentil, and the like) or oilseeds (rapeseed, soybean, sesame, cotton, and the like), said extract containing proteins in solution or in colloidal suspension, which can coagulate in acid medium. Finally, the term "milk" also refers to mixtures of animal milks and of vegetable milks.

Protein matters with a high nutritive value, according to the recommended rations, such as casein and proteins from egg, from soybean, from pea, from bean, from lentils, from chickpea, from lupin, from carob, from rapeseed or originating from other sources recognized for their nutritive values are particularly indicated in the context of the present invention (FAO/WHO, Protein Quality Evaluation, No. 51, Rome 1991). These proteins can contain a balanced and high content of each of the amino acids which are essential for the body, such as lysine, tryptophan, leucine, isoleucine, valine, phenylalanine, methionine and threonine, for example.

Preferably, the untreated protein matter comprises slowly digested proteins, i.e., proteins which, when ingested by rats weighing 140 to 200 g, can lead to a disappearance of half the ingested nitrogen present in the digestive tract in more than 80 minutes. Proteins which coagulate in the stomach, such as casein, are most frequently slowly digested proteins. Specifically, it is known that the rate of digestion of food proteins is controlled by the stomach, and more specifically by gastric emptying (Gaudichon et al., American Institute of Nutrition, Milk and Yoghurt Digestion 1970–1977, 1994). The coagulum formed in the stomach in this way has trouble leaving, which delays the digestion of the protein.

To implement the present method, this protein matter is then treated with transglutaminase to catalyze polymerization, deamidation, and amine-incorporation reactions (Nielsen, Food biotechnol., 9, 119–156, 1995). The treatment conditions can vary according to the requirements of the present invention. As a general rule, the proteins are suspended in an aqueous medium in a proportion of 1 to 30% by weight, transglutaminase is added in a proportion of 100 to 100,000 units/L, the suspension is subjected to optimal conditions for hydrolysis (pH 7, 5000 units/L), and the enzyme is inactivated by heat and/or by hydrostatic pressure of 300 to 1100 MPa (see EP 686352 and EP 748592 of S.P.N.).

Anionic polysaccharides, in particular chosen from alginates, xanthan, gum arabic, pectins, kappa-carrageenans, iota-carrageenans, lambda-carrageenans, carboxymethylcellulose, sulfated dextrans and/or gellan gum, are then added to the protein matter, before or after treatment with the transglutaminase. The treatment conditions can vary according to the requirements of the present invention. As a general rule, between 0.05 and 30% by w/v of anionic polysaccharides are added.

The conditions for treating the protein matter should preferably be chosen so as to reach a level of acceleration of the rate of digestion of the protein matter such that, when the treated protein matter is administered orally to rats weighing 140 to 200 g, it leads to a disappearance of half the ingested nitrogen present in the digestive tract in less than 70 minutes, for example.

The protein matter thus treated can be used advantageously for preparing a food or pharmaceutical composition intended for oral administration to a mammal, to induce a plasmatic postprandial peak of amino acids, and, as a result, to accomplish one or more of the following: to modulate the postprandial protein gain; to limit the problems linked to gastrointestinal motility disorders; to limit the postprandial sensations of nausea in pregnant women; and/or to limit the postprandial risks of regurgitation and/or gastro-esophageal reflux.

The present use is not however limited to a protein matter treated according to the invention. Specifically, other treatments can also induce an acceleration of the rate of digestion of a protein matter. The present use thus also aims to use any protein matters which have been pretreated so as to transform the slowly digested proteins that it contained into rapidly digested proteins which have at least substantially conserved the same initial molecular weight.

For this, one of the abovementioned protein matters, which has however been treated with transglutaminase, such as those described in WO 97/05785 (Milupa GmbH) can be used, for example. In this case, the molecular weight of the proteins thus treated increases as a result of the polymerization of the proteins.

It is also possible to use only mixtures of proteins and of anionic fibers, such as those described in U.S. Pat. No. 5,126,332, in particular making use of the above-mentioned polysaccharides, for example. In this case, the molecular weight of the proteins thus treated remains identical, but their physicochemical properties are modified as a result of the interaction with the polysaccharides.

Preferably, to implement the present methods, a protein matter which initially contained slowly digested proteins is used, i.e., proteins which, when ingested by rats weighing 140 to 200 g, lead to a disappearance of half the ingested nitrogen present in the digestive tract, in more than 80 minutes.

Protein matters which have a high nutritive value are also particularly indicated. These matters can be exploited in people with a physiological requirement for rapidly digested proteins, such as patients who are in a postoperative or post-traumatic period, children or sportspersons who have just undergone effort, or in people who have a physiological aversion to consuming slowly digested proteins, such as elderly people, people suffering from anorexia, or pregnant women subject to nausea.

The food or pharmaceutical compositions which comprise these accelerated-digestion protein matters are preferably used in the context of diets, or even of therapeutic treatments, for preventing or treating problems linked to specific pathological or physiological states. The conditions governing these diets depend in fact on the categories of people concerned. As a general rule, it will be considered that the composition comprises an amount of protein matter which is sufficient and effective in inducing a postprandial plasmatic peak of amino acids.

More particularly, these compositions are aimed at athletes who are looking to increase their body mass, and more specifically their muscle mass. These compositions can thus comprise a source of proteins which represents 15% to 100% of the total energy. This source can consist essentially of at least one of the treated protein matters described above. Preferably, these compositions comprise treated casein, this casein comprising about 22% valine, leucine and isoleucine, the amino acids being used in the muscle as energetic substrates (Kasperek et al., Am. J. Physiol., 252, E33–37, 1987), and allowing carbohydrate stores to be saved (Blomstrand et al., Nutrition., 12, 485–490, 1996).

Children who exercise physically also have the same physiological requirements as an athlete, particularly after an intense effort. The food compositions for children are preferably formulated to be particularly revitalizing. For this, they comprise, in addition to the source of proteins, a source of carbohydrates which can be rapidly assimilated, lipids, as well as mineral salts and vitamins.

Finally, patients who are in a postoperative or posttraumatic period also have considerable physiological requirements for amino acids. The food compositions are preferably formulated to also be revitalizing. For this, they also comprise, in addition to the source of proteins, a source of carbohydrates which can be rapidly assimilated, lipids, as well as mineral salts and vitamins.

Gastrointestinal motility disorders are often associated with ageing and with pathological states such as anorexia, diabetes, the presence of a gastric carcinoma, neurological disorders (e.g., Parkinson's disease), drug dependency, alcoholism, and the like. The time required for gastric emptying and digestion in these people is abnormally high, which leads to symptoms of anorexia, nausea, and vomiting. These people can thus also have a sensation of satiety which is too strong and protracted after a meal, such that they have difficulties in eating regularly and sufficiently. A composition comprising proteins of high nutritive value, which are rapidly evacuated from the stomach and which are rapidly digested, participates in the elimination of these problems. This composition can thus comprise a source of proteins which represents 10% to 30% of the total energy. This source of proteins can essentially consist of at least one of the treated protein matters described above.

During pregnancy, because of the increase in body mass due to the conception (foetus, placenta) and the hypertrophy of various maternal tissues (uterus, breasts, extracellular fluids), the energy and protein requirements are greater. Many pregnant women suffer from temporary nausea, however, and this hinders them from maintaining a balanced diet. A composition comprising proteins of high nutritive value, which are rapidly evacuated from the stomach and which are rapidly digested, participates in the reduction or elimination of these problems. This composition can thus comprise a source of proteins which represents 10% to 30% of the total energy. This source of proteins can essentially consist of at least one of the treated protein matters described above.

Problems of gastro-esophageal reflux are often observed in pregnant women, newborn babies or premature babies, in particular after ingestion of milk. Current treatments consist in thickening foods and/or in accelerating gastric emptying and in increasing the tonus of the gastro-esophageal sphincter by means of medicaments. The compositions according to the invention are particularly suitable for preventing, or even treating, these problems. These compositions can thus comprise a source of proteins which represents 10% to 40% of the total energy. This source of proteins can essentially consist of at least one of the treated protein matters described above.

More particularly, the compositions comprising anionic polysaccharides have a three-fold advantage for treating problems of reflux. Firstly, the protein matters have a viscosity which limits problems of reflux. Secondly, these protein matters are rapidly removed from the stomach, which also limits problems of reflux. Thirdly, these protein matters are very easily digested.

Finally, newborn babies or patients fed by the enteral route also have problems of regurgitation, which can lead to obstruction of the respiratory pathway. The enteral compositions use complex mixtures of micro- and macro-nutriments in order to improve the nutritional state of the patients. To date, three sources of amino acids have generally been used for these patients, i.e. intact proteins, hydrolyzed proteins (peptides) and amino acids. Amino acids and peptides have an unpleasant taste, and cause an increase in gastrointestinal osmolarity, this parameter leading to the appearance of diarrhea. In addition, the nutritive value of free amino acids is not comparable to that of intact proteins. For intact proteins, most of the enteral compositions use casein. Unfortunately, it coagulates in the stomach and gastric emptying is thus protracted. The present invention aims to use a composition with a good taste, comprising nonhydrolyzed protein matters which are digested very rapidly. This composition can thus comprise a source of proteins which represents 15% to 25% of the total energy. This source of proteins can essentially consist described above.

The food or pharmaceutical compositions comprise, preferably, a source of carbohydrates which provides 50 to 70% of the total energy. Carbohydrates, in particular after a physical effort, after a postoperative trauma, during pregnancy and in newborn babies, are important nutrients for restoring sugar stores, and avoiding hypoglycemia. All the carbohydrates can be used, in particular maltodextrins, saccharose, lactose and glucose.

The food or pharmaceutical compositions can comprise a source of lipids which provides 15 to 35% of the total energy. Vegetable oils are recommended, in particular those originating from soybean, oil palm, coconut palm, sunflower, etc. Minerals, vitamins, salts, emulsifiers or flavor-enhancing compounds can also be added to the compositions, according to the desired requirements.

The food or pharmaceutical compositions can be prepared in all kinds of ways, the manufacturing steps generally including a dispersion of the ingredients in water, and a pasteurization. The compositions can be prepared in the form of drinks or of liquid concentrates, or in the form of a powder which can be reconstituted in water, etc.

EXAMPLES

The present invention is described in more detail below with the aid of the further description which will follow, which refers to examples for preparing food compositions according to the invention. These examples are preceded by a brief description of the figures. The percentages are given by weight, except where otherwise indicated. It goes without saying, however, that these examples are given as an illustration of the subject of the invention, of which they in no way constitute a limitation.

Example 1

Treatment with Transglutaminase

A suspension comprising 10% by weight/volume of micellar casein is treated with 5 units/ml of microbial transglutaminase (Ajinomoto) at pH 7, at 50° C., and for 1 hour, and the enzyme is then inactivated by heat treatment at 80° C. for 10 min.

The casein suspension thus polymerized does not gel, and remains stable even at pH 3. For comparison, native micellar casein precipitates at pH 3, forming large aggregates.

The rate of digestion of casein thus treated is determined in vivo in Sprague-Dawley male rats (IffaCredo, France) weighing 140 to 200 g. After an acclimatization period of 2 days, the rats are separated, they are made to fast for 22 h, they are force-fed with 5 ml of a suspension containing 5% by weight treated casein, and various batches of rats are then put to sleep at 0 min (5 rats), 30 min (2 rats), 60 min (2 rats), 90 min (2 rats) 120 min (2 rats), 150 min (2 rats), 180 min (2 rats), 210 min (2 rats), 240 min (2 min (5 rats) after the gavage. The animals are sacrificed, the abdominal cavity is opened, blood is taken from the portal vein and the dorsal aorta, and the gastric and intestinal contents are recovered by washing the various mucous membranes with a suspension comprising 0.9% sodium chloride.

The blood samples are mixed with heparin, they are centrifuged, the plasma samples are deproteinized with a sulfosalicylic acid solution (3.6% final conc.), and the samples are frozen until analysis of their amino acid content with a Beckman-6300 analyzer.

The gastric and intestinal contents are kept cold, and their total nitrogen content is analyzed using the Kjedah method.

For comparison, 5 rats which have undergone the same protocol without the gavage step are used to determine the basal values of the endogenous content of gastrointestinal nitrogen and of plasmatic amino acids.

Figure 1:
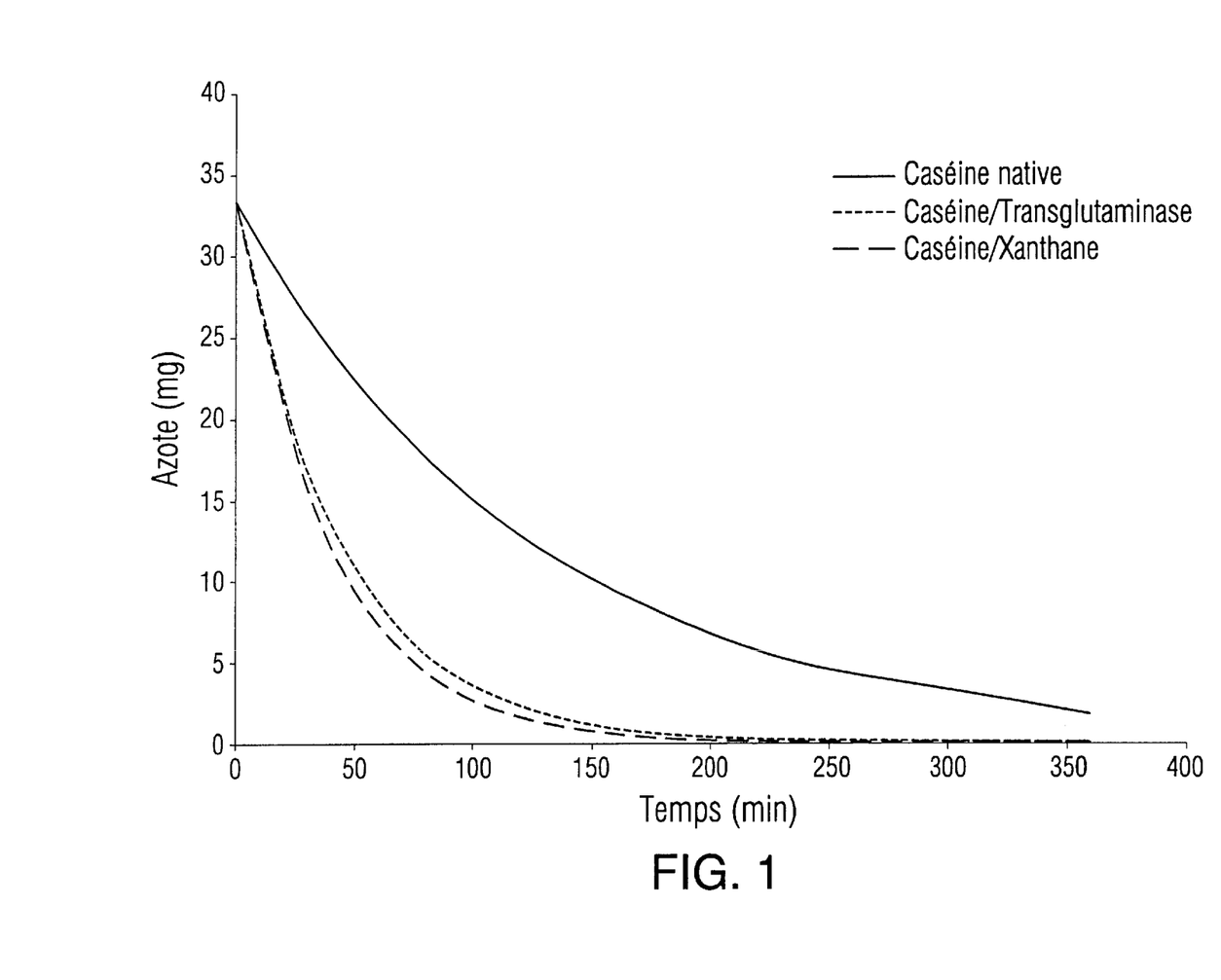
FIG. 1 represents the evolution of the gastric nitrogen content, as a function of time, in rats fed on native casein, on casein treated with transglutaminase, or on a mixture of native casein and xanthan.

The kinetics of the gastric nitrogen content, represented in FIG. 1, show that half the ingested nitrogen disappears from the stomach in 35 min for the treated casein, whereas it disappears in 87 min for the native casein. In addition, against all expectations, the treated casein always remains liquid in the stomach, without forming a coagulum. The parameters of these kinetics are presented in Table I in Example 2.

Figure 2:
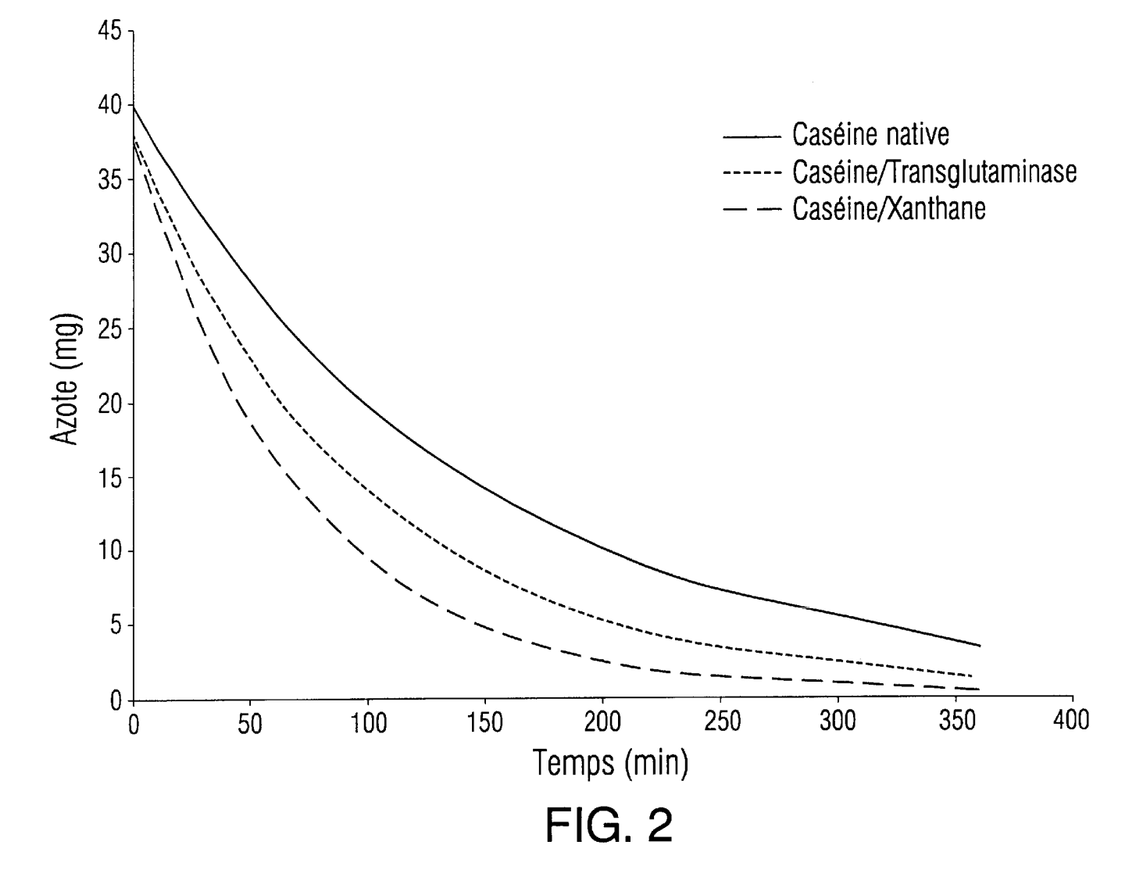
FIG. 2 represents the evolution of the gastrointestinal nitrogen content (digestion kinetics), as a function of time, in rats fed on native casein, on casein treated with transglutaminase, or on a mixture of native casein and xanthan.

The kinetics of digestion are obtained by adding the values of the content of gastric nitrogen and of intestinal nitrogen. The results represented in FIG. 2 show that half the ingested nitrogen disappears from the digestive tract in 69 min for the treated casein, whereas it disappears in more than 99 min for the native casein. The parameters of these kinetics are presented in Table 1 in Example 2.

The kinetics of appearance of amino acids in the blood, represented in FIG. 3, show the rapid appearance of a plasmatic peak of amino acids for the treated casein.

Example 2

Treatment with Anionic Polysaccharides

Several suspensions are prepared comprising 0.1 to 10% weight/volume of an anionic polysaccharide chosen from alginates (PROTANAL LF20®, Pronova Biopolymers), pectins (LM12CG®, Pomosin), xanthan (KETROL F®, Kelco), guar gum (GUARDAN 178, Grinsted) and carboxymethylcellulose (No. 99-7H4XF, Aqualon), gum arabic (FIBREGUM® AS IRX 29830, CNI, France), and then 5% micellar casein is added.

At pH 3, the suspensions precipitate and form a coagulum of mucilaginous consistency. The appearance of this coagulum is very different from that obtained, at pH 3, with the native micellar casein, which forms clots with a porous appearance.

The rate of digestion of the caseins thus treated is determined in vivo in rats. The results are comparable to those presented in Example 1. As an indication, the results obtained more particularly with xanthan are set out below.

To this end, the kinetics of the gastric nitrogen content, represented in FIG. 1, show that half the ingested nitrogen disappears from the stomach in 28 min for the mixture of casein and of xanthan, whereas it disappears in 87 min for the native casein. In addition, against all expectations, the treated casein always remains liquid in the stomach, without forming a coagulum. The parameters of these kinetics are presented in Table 1 below.

The kinetics of digestion, represented in FIG. 2, show that half the ingested nitrogen disappears from the digestive tract in 50 min for the mixture of casein and of xanthan, whereas it disappears in more than 99 min for the native casein. The parameters of these kinetics are presented in Table 1 below.

The kinetics of appearance of amino acids in the blood, represented in FIG. 3, show the rapid appearance of a plasmatic peak of amino acids.

TABLE 1

Rate $(K)^1$ and $t½^2$ of the gastric emptying and of the digestion for the treated and native caseins.

| Casein | Gastric emptying | | Digestion | |
|---|---|---|---|---|
| | $K(\times 10^{-3},$ $min^{-1})$ | $t½(min^{-1})$ | $K(\times 10^{-3},$ $min^{-1})$ | $t½(min^{-1})$ |
| Native | 8 | 87 | 7 | 99 |
| Casein-transglutaminase | 22 | 32 | 10 | 69 |
| Casein-xanthan | 25 | 28 | 14 | 50 |

[1]Calculated from the equation $N_t = Ae^{-Kt}$, or $N_t$ = the amount of nitrogen at a time t which remains in the stomach or in the gastrointestinal system, A = the nitrogen content at t = 0, and K = the rate of digestion or of gastric emptying.
[2]Calculated from the equation $t½ = (\ln 2)/K$, or $t½$ = the time required for half the nitrogen to be removed from the stomach or to be digested.

Example 3

Treatment with Transglutaminase and Polysaccharides

1% xanthan (KETROL F®, Kelco) is added to the suspension of micellar casein treated with transglutaminase according to Example 1. The rate of digestion of the casein thus treated is determined in vivo in rats, as described in Example 1. The results are comparable to those obtained in Examples 1 and 2.

Example 4

Food Composition for Infants

A food composition for infants is prepared in the form of a soluble powder which has the composition defined in Table 2 below. This powder is used in a proportion of 13% in water, which corresponds to an energy content of the order of 70 kcal/100 ml.

To prepare this powder, water is purified by reverse osmosis, it is heated to 70° C., a source of proteins and a source of carbohydrates are added to it, a source of lipids in which liposoluble vitamins have been predispersed is also added to it, the mixture is heated to 80° C. for 5 min by injection of steam, it is cooled to 60°, water-soluble vitamins and minerals are added to it, it is homogenized in 2 steps at 10 MPA and then at 7 MPa, it is dried by spraying under a stream of warm air until a water content of 4% is attained, and it is then reduced to a fine powder which is soluble in water.

TABLE 2

| PROTEINS | 2.3 G/100 Kcal |
|---|---|
| casein treated according to Example 1 | 40% |
| whey | 60% |
| CARBOHYDRATES | 10 g/100 Kcal |
| lactose | 100% |
| LIPIDS | 5.5 g/100 Kcal |
| milk fat | 70% |
| canola oil | 15% |
| corn oil | 14% |
| soybean lecithin | 1% |
| MINERALS | (mg/100 Kcal) |
| sodium | 24 |
| potassium | 100 |

TABLE 2-continued

| | |
|---|---|
| chloride | 67 |
| calcium | 65 |
| phosphorus | 32 |
| magnesium | 7 |
| iron | 1.4 |
| zinc | 0.7 |
| copper | 0.07 |
| VITAMINS | (for 100 Kcal) |
| vitamin A | 300 IU |
| vitamin D | 35 IU |
| vitamin E | 1.3 IU |
| vitamin K | 8.2 μg |
| vitamin C | 8.1 mg |
| thiamine | 60 μg |
| riboflavin | 130 μg |
| niacin | 760 μg |
| vitamin B6 | 70 μg |
| folic acid | 10 μg |
| pantothenic acid | 460 μg |
| vitamin B12 | 0.3 μg |
| biotin | 2.5 μg |
| choline | 8 mg |
| inositol | 5 mg |

Example 5

Food Supplement for Sportspersons

A liquid food supplement is prepared which is intended for sportspersons, and more particularly for people who have just performed physical activity. The manufacturing process is similar to that described in Example 4. This nutritional liquid product has an energy content of 60 Kcal/100 ml. The composition of this formula is detailed in Table 3 below.

TABLE 3

| PROTEINS | 5 g/100 Kcal |
|---|---|
| casein treated according to Example 1 | 100% |
| CARBOHYDRATES | 10 g/100 Kcal |
| maltodextrins | 64% |
| sucrose | 36% |
| MINERALS | mg/100 ml |
| sodium | 20 |
| potassium | 45 |
| calcium | 15 |
| magnesium | 7 |
| phosphorus | 17 |
| iron | 0.5 |
| iodine | 0.01 |
| selenium | 0.02 |
| VITAMINS | mg/100 ml |
| C | 30 |
| B1 | 0.25 |
| B2 | 0.33 |
| B5 | 1.4 |
| B6 | 0.35 |
| B12 | 0.8 |
| biotin | 28 |
| D3 | 0.8 |
| K | 8 |
| PP | 3.5 |

Example 6

Enteral Composition

A liquid enteral composition, which has the ingredients defined in Table 4 below, is prepared in the same way as in Example 4, with the difference that the mixture is homogenized at 150° C. by injection of steam, it is cooled at 75° C., and it is packaged aseptically in containers. This composition has an energy content of 100 Kcal/100 ml.

TABLE 4

| PROTEINS | 6.5 g/100 ml |
|---|---|
| casein treated according to Example 2 (xanthan: casein, ratio 5:1) | 100% |
| CARBOHYDRATES | 11.3 g/100 ml |
| corn syrup solids | 66% |
| sucrose | 34% |
| LIPIDS | 3.4 g/100 ml |
| coconut oil | 50% |
| canola oil | 30% |
| corn oil | 14% |
| soybean lecithin | 6% |
| MINERALS | (mg/100 ml) |
| calcium | 80 |
| potassium | 150 |
| phosphorus | 70 |
| chloride | 130 |
| sodium | 87.6 |
| zinc | 1.4 |
| magnesium | 40 |
| iron | 1.2 |
| copper | 0.2 |
| manganese | 0.3 |
| selenium | 0.1 |
| chromium | 0.004 |
| molybdenum | 0.012 |
| iodine | 0.01 |
| VITAMINS | (for 100 ml) |
| vitamin A | 400 IU |
| β-carotene | 0.2 mg |
| vitamin D | 30 IU |
| vitamin E | 4 IU |
| vitamin C | 15 mg |
| vitamin K | 8 μg |
| thiamine | 0.2 mg |
| riboflavin | 0.25 mg |
| niacin | 2.4 mg |
| pyridoxine | 0.4 mg |
| folic acid | 50 μg |
| pantothenic acid | 1.4 mg |
| vitamin B12 | 0.8 μg |
| biotin | 40 μg |
| choline | 45 mg |

Example 7

Nutritional Composition for Children

A liquid nutritional composition for children chocolate-flavored milk. This composition has an energy content of 75 Kcal/100 ml, and its constituents are specified in Table 5 below. It is prepared in the same way as in Example 4, with the difference that the mixture is homogenized at 150° C. by injection of steam, it is cooled to 75° C., and it is packaged aseptically in TETRA-BRICK® packages.

TABLE 5

| PROTEIN | 4 g/100 Kcal |
|---|---|
| casein treated according to Example 1 | 100% |
| CARBOHYDRATES | 15 g/100 Kcal |
| corn syrup solids | 62% |
| sucrose | 38% |

TABLE 5-continued

| | | |
|---|---|---|
| LIPIDS | 2.5 g/100 Kcal | |
| milk fats | 40% | |
| corn oil | 42% | |
| cocoa butter | 10% | |
| soybean lecithin | 8% | |
| MINERALS | (mg/100 Kcal) | |
| calcium | 50 | |
| phosphorus | 30 | |
| zinc | 0.3 | |
| magnesium | 4 | |
| iron | 0.5 | |
| selenium | 0.02 | |
| zinc | 0.7 | |
| iodine | 0.01 | |
| VITAMINS | (for 100 Kcal) | |
| vitamin A | 250 IU | |
| vitamin D | 50 IU | |
| vitamin E | 1 IU | |
| vitamin C | 8 mg | |
| thiamine | 60 µg | |
| riboflavin | 130 µg | |
| niacin | 760 µg | |
| vitamin B6 | 70 µg | |
| folic acid | 10 µg | |
| pantothenic acid | 460 µg | |
| vitamin B12 | 0.8 µg | |

Example 8

Milk Substitute for Pregnant Women

A powdered composition is prepared, which is intended for substituting cow's milk for the nutrition of pregnant women suffering from problems of nausea and/or vomiting. This powder can be reconstituted in water in a proportion of 10.7%. The energy content of the reconstituted composition is of the order of 50 kcal/100 ml. The ingredients of the composition are specified in Table 6 below. This composition is prepared in the same way as in Example 4.

TABLE 6

| | |
|---|---|
| PROTEINS | 4.0 g/100 Kcal |
| treated casein from Example 3 (xanthan:casein, 1:5) | 40% |
| whey | 60% |
| CARBOHYDRATES | 14.8 g/100 Kcal |
| maltodextrin | 55% |
| sucrose | 45% |
| LIPIDS | 2.7 g/100 Kcal |
| milk fat | 20% |
| corn oil | 74% |
| soybean lecithin | 6% |
| MINERALS | (mg/100 Kcal) |
| calcium | 280 |
| potassium | 60 |
| phosphorus | 140 |
| chloride | 60 |
| sodium | 30 |
| zinc | 6 |
| magnesium | 23 |
| iron | 5 |
| iodine | 0.05 |
| VITAMINS | (for 100 Kcal) |
| vitamin A | 250 IU |
| vitamin D | 120 IU |
| vitamin E | 4.7 IU |

TABLE 6-continued

| | |
|---|---|
| vitamin C | 35 mg |
| thiamine | 0.4 mg |
| riboflavin | 0.4 mg |
| niacin | 5 mg |
| pyridoxine | 0.8 mg |
| folic acid | 150 µg |
| pantothenic acid | 1.2 mg |

Example 9

Nutritional Composition for Elderly People

A powdered composition is prepared which is intended for substituting cow's milk for the nutrition of elderly people suffering from gastrointestinal motility disorders. This powder can be reconstituted in water in a proportion of 10.7%. The energetic density of the reconstituted composition is of the order of 50 kcal/100 ml. The ingredients of the composition are presented in Table 7 below. This composition is prepared in the same way as in Example 4.

TABLE 7

| | |
|---|---|
| PROTEINS | 3.0 g/100 Kcal |
| casein treated according to the method of Example 3 with a kappa-carrageenan (kappa-carrageenan: casein, 1:5) | 45% |
| whey | 55% |
| CARBOHYDRATES | 15.3 g/100 Kcal |
| maltodextrin | 70% |
| sucrose | 30% |
| LIPIDS | 3.0 g/100 Kcal |
| milk fats | 20% |
| corn oil | 74% |
| soybean lecithin | 6% |
| MINERALS | (mg/100 Kcal) |
| calcium | 200 |
| phosphorus | 120 |
| chloride | 50 |
| sodium | 20 |
| zinc | 4 |
| magnesium | 20 |
| iron | 4 |
| iodine | 0.05 |
| VITAMINS | (for 100 Kcal) |
| vitamin A | 150 IU |
| vitamin D | 120 IU |
| vitamin E | 3 IU |
| vitamin C | 40 mg |
| thiamine | 0.4 mg |
| riboflavin | 0.3 mg |
| niacin | 5 mg |
| pyridoxine | 0.75 mg |
| folic acid | 75 µg |
| pantothenic | 1 mg |

What is claimed is:

1. A method for accelerating the rate of digestion of milk protein matter, which comprises treating milk protein matter with transglutaminase under conditions sufficient to catalyze polymerization, deamidation, or amine-incorporation reactions in the milk protein matter to obtain treated milk proteins, optionally followed by the mixing of the treated milk proteins with one or more anionic polysaccharides to form a mixture, wherein the treated milk proteins have an accelerated rate of digestion compared to the untreated milk protein matter.

2. The method of claim 1, wherein the anionic polysaccharide is one or more of an alginate, xanthan, gum arabic, pectin, kappa-carrageenan, iota-carrageenan, lambda-carrageenan, carboxymethylcellulose, sulfated dextran, gellan gum, or mixtures thereof.

3. The method of claim 1, wherein the milk protein matter comprises casein.

4. The method of claim 1, wherein the milk protein matter comprises slowly digested milk proteins which, when ingested by rats weighing from 140 grams to 200 grams, lead to a disappearance of half the ingested nitrogen present in the digestive tract in more than 80 minutes.

5. The method of claim 4, wherein the milk protein matter is treated with transglutaminase followed by the addition of the anionic polysaccharide(s) to provide a treated mixture that contains rapidly digested milk proteins which, when ingested by rats weighing from 140 grams to 200 grams, leads to a disappearance of half the ingested nitrogen present in the digestive tract in less than 70 minutes.

6. The method of claim 5, wherein the rapidly digested milk proteins have at least substantially the same molecular weight as that of the slowly digested proteins.

7. A treated milk protein matter produced by the method according to claim 5, and having an accelerated rate of digestion such that when the treated milk protein matter is ingested by rats weighing from 140 grams to 200 grams, half the ingested nitrogen present in the digestive tract disappears in less than 70 minutes, and the treated milk protein matter has at least substantially the same molecular weight as that of the slowly digested milk proteins.

8. The treated protein matter mixture of claim 7, wherein the treated milk protein matter comprises treated casein and which further comprises one or more of a source of carbohydrates which can be rapidly assimilated, a lipid, a mineral salt, a vitamin or mixtures thereof.

9. A method of modulating postprandial protein gain in mammals by oral administration of a composition comprising a therapeutically effective amount of the treated milk protein matter of claim 1 to a mammal in need of such treatment.

10. The method of claim 9, wherein the oral administration of composition comprises consumption by patients in a postoperative or post-traumatic period, by children, or by sportspersons, such that their protein mass is maintained, restored, or developed.

11. The method of claim 9, wherein the composition is a revitalizing composition for further maintaining, restoring, or developing muscle mass.

12. A method of reducing problems linked to gastrointestinal motility disorders in mammals by oral administration of a composition comprising a therapeutically effective amount of the treated milk protein matter of claim 1 to a mammal in need of such treatment.

13. The method of claim 12, wherein the problems to be reduced include having a sensation of satiety which is too strong and protracted after a meal, resulting in difficulties in eating regularly and sufficiently.

14. The method of claim 12, wherein the oral administration of composition comprises consumption by elderly people or people with anorexia, diabetes, the presence of a gastric carcinoma, neurological disorders, drug dependency, or alcoholism.

15. A method of limiting nausea in pregnant women by oral administration of a composition comprising a therapeutically effective amount of milk protein matter that is treated to have an accelerated rate of digestion, wherein the composition is administered to a woman in need of such treatment, wherein the protein matter is treated with transglutaminase under conditions sufficient to catalyze polymerization, deamidation, or amine-incorporation reactions in the milk protein matter, or is mixed with one or more anionic polysaccharides, to thus obtain treated protein matter having an accelerated rate of digestion compared to untreated protein matter.

16. A method of limiting risk of regurgitation and/or gastro-esophageal reflux in mammals by oral administration of a composition comprising a therapeutically effective amount of milk protein matter that is treated to have an accelerated rate of digestion, wherein the composition is administered to a mammal in need of such treatment, wherein the protein matter is treated with transglutaminase under conditions sufficient to catalyze polymerization, deamidation, or amine-incorporation reactions in the milk protein matter, or is mixed with one or more anionic polysaccharides, to thus obtain treated protein matter having an accelerated rate of digestion compared to untreated protein matter.

17. The method of claim 16, wherein the composition further provides nutritive components for nutrition of children, pregnant women, or patients fed by an enteral route.

18. The method of claim 17, wherein the nutritive components comprise one or more of a source of carbohydrates which can be rapidly assimilated, a lipid, a mineral salt, a vitamin or mixtures thereof.

19. A food or pharmaceutical composition comprising the treated protein matter of claim 5.

20. The food or pharmaceutical composition of claim 19, which further comprises one or more of a source of carbohydrates which can be rapidly assimilated, a lipid, a mineral salt, a vitamin or mixtures thereof.

* * * * *